US008133188B2

(12) United States Patent
Hatch

(10) Patent No.: US 8,133,188 B2

(45) Date of Patent: Mar. 13, 2012

(54) ESTRUS DETECTION DEVICE

(76) Inventor: Ira Steven Hatch, Bountiful, UT (US)

( * ) Notice: Subject to any disclaimer, the term of this patent is extended or adjusted under 35 U.S.C. 154(b) by 0 days.

(21) Appl. No.: 12/657,258

(22) Filed: Jan. 15, 2010

(65) Prior Publication Data

US 2011/0178423 A1 Jul. 21, 2011

(51) Int. Cl.
*A61B 10/00* (2006.01)

(52) U.S. Cl. ........................................................ 600/551

(58) Field of Classification Search ................... 600/551
See application file for complete search history.

(56) References Cited

U.S. PATENT DOCUMENTS

| | | | | |
|---|---|---|---|---|
| 3,076,431 | A * | 2/1963 | Rule et al. | 600/551 |
| 3,158,134 | A * | 11/1964 | Larson | 600/551 |
| 3,774,022 | A * | 11/1973 | Dubrow et al. | 362/34 |
| 4,206,766 | A | 6/1980 | Bielka | |
| 4,239,018 | A * | 12/1980 | Griffin et al. | 600/551 |
| 4,635,587 | A | 1/1987 | Leonardo | |
| 4,696,258 | A * | 9/1987 | Magrath et al. | 600/551 |
| 5,566,679 | A * | 10/1996 | Herriott | 600/551 |
| 6,342,041 | B1 | 1/2002 | Saint-Ramon | |
| 7,137,359 | B1 * | 11/2006 | Braden | 119/854 |

* cited by examiner

*Primary Examiner* — Max Hindenburg
*Assistant Examiner* — Charles Becker
(74) *Attorney, Agent, or Firm* — Pearl Cohen Zedek Latzer, LLP

(57) ABSTRACT

Embodiments of the present invention are directed to a device and method for identifying estrus in production animals by detecting one or more standing mounts with a single device.

21 Claims, 2 Drawing Sheets

ESTRUS DETECTION DEVICE

CROSS REFERENCE TO RELATED APPLICATION

Not applicable

STATEMENT REGARDING FEDERAL SPONSORSHIP

The present invention was not made or developed with Federal sponsorship.

FIELD OF THE INVENTION

The present invention relates to an apparatus for detecting standing heats in cows and other animals. The invention further relates to a method for using such an apparatus in animals to detect multiple estruses.

BACKGROUND

Description of Prior Art

The artificial insemination of dairy and beef cows is an important means for enhancing productivity through rapid genetic improvement. Artificial insemination of semen from the top industry sires with the most valuable traits can be used much more widely than would be the case if only natural service were available. However, successful insemination programs require herdsmen to accurately determine the timing of estrus so that artificial insemination can lead to conception. In cows, insemination must occur during or shortly after a relatively brief period of sexual receptivity to achieve conception. This period of sexual receptivity is referred to alternatively as the estrus period, estrus or heat.

An objective with artificial insemination is to inseminate a cow the minimum number of times possible to reduce semen and labor costs while still achieving pregnancy. Dairy cows are managed such that they are ideally bred and become pregnant approximately 60 days after calving to maximize the number of calves produced during the economic life of the cow. Pregnancy is necessary to bring about physiological changes which provide for the onset of lactation following a drying off period.

A basic understanding of fertility and the estrus cycle of the cow is necessary for appreciation of existing management problems and solutions. The estrus period in cattle occurs approximately every 21 days in non-pregnant or open cows. The cow remains in estrus for approximately 12-24 hours. The cow ovulates approximately 14 hours after estrus. The time of ovulation is the optimum time for artificial insemination. If the cow is successfully inseminated, she will become pregnant for approximately 280 days.

If the desired estrus cycle, for example, the first postpartum estrus cycle, is not detected or if the cow is not successfully bred during a particular cycle, the cow cannot normally be bred for at least another 21 days unless hormone therapy in instituted.

It is known that cattle exhibit several behavioral and physiological characteristics which are specific to the estrus phase of their cycles, or which occur very near estrus. Physiological indications that an animal is in estrus include increased blood flow to the reproductive tract, changes in the impedance of reproductive tract fluids, elevated body temperature, and changes in blood hormone levels.

Behavioral indications that cattle are in estrus include nervousness, increased physical activity and mobility, and increased vocalization (bawling). Cattle also exhibit certain behavior associated with mounting. During estrus there is an increased frequency of mounting of other cattle by the animal in heat.

Another characteristic of cattle in estrus which is particularly important to this invention is that a cow in heat will allow itself to be mounted and remain mounted by other cattle. This behavior, termed "standing to be mounted" is mating behavior exhibited by the cow in heat. Although cattle are mounted by other cattle at times outside of estrus, the cow being mounted will maintain a relatively prolonged mounted standing posture only during estrus. When a cow is not in estrus, it will not allow prolonged mounting by other cattle in the herd, and will walk out or bolt from under a cow or bull which is attempting to mount. This behavior has given rise to the term "standing heat" which indicates the period of actual estrus during which fertilization and conception can occur and the cow will stand to be mounted. Standing to be mounted is also an indication of estrus in other animal species, such as sheep.

Artificial insemination following accurate detection of estrus can lead to improved conception rates. Subsequent observations of signs of estrus usually indicate the cow failed to conceive following the first insemination or that she failed to maintain her pregnancy and will require additional inseminations. A cow that is pregnant does not cycle and therefore does not exhibit further signs of heat or estrus.

A common method of detecting heat in cattle is to apply chalk to the tail heads of cows being monitored. This approach involves applying a grease crayon-like mark to the tail head or rump area of the cow. Upon receiving mounting activity the mark is diminished or even completely rubbed off. While simple to implement, this approach suffers from the difficulty in differentiating between a standing heat and the normal mounting behavior that also occurs with cows that are mounted and immediately bolt. Chalk is removed or disturbed during any mounting activity, not just during a standing heat.

Other methods of detecting mounting activity rely on gluing mechanical or electronic devices to the tail head of a cow. In Leonardo, U.S. Pat. No. 4,635,587, one such electronic monitoring system is described. U.S. Pat. No. 6,342,041 describes an electronic monitor that is glued to the tail head of a cow to provide a visual reading of electronically monitored mounting activity. U.S. Pat. No. 4,206,766 discloses a mechanical device glued to the tail head which is tripped by mounting behavior upon the cow. The signaling mechanism is a flag that pops up, letting the herdsman know a mount has occurred. Like chalk, several of these devices fail to differentiate between a mount and a standing mount.

A mechanical device that effectively differentiates between a mount and a standing mount is the KAMAR® HEATMOUNT® detector, described in U.S. Pat. No. 3,076,431. As with most estrus detection devices, the KAMAR® detector is glued to the tail head of a cow and detects a physical mounting behavior. However, the detector contains a simple timing mechanism to identify a standing mount. The device consists of a dye-colored indicator fluid that is expressed from a collapsible fluid storage reservoir through a reservoir outlet into a timing chamber when pressure from mounting activity is applied. The detector is referred to a being triggered when the dye-colored indicator fluid spills out of the timing cylinder and turns the wicking means red. The KAMAR® detector is triggered only if a standing mount of several seconds has occurred. When a cow with the device attached is not receptive to a sustained mount and instead bolts, any indicator fluid initially expressed from the collapsible reservoir through the reservoir outlet into the timing chamber by the weight of the cow during the abbreviated mounting period is drawn back into the reservoir by action of the collapsed tubing returning to its natural cylindrical shape. This prevents the indicator fluid from spilling from the timing chamber onto the wicking means and turning red. While such a device with a timing chamber gives a good indication of standing heat, it has an important shortcoming: it can be used only once, which significantly limits its usefulness relative to the present invention.

Estrus detection devices are not limited to the identification of just the first heat during the breeding period. After inseminating a cow following the first detection of a standing heat, many herdsmen glue a second estrus detection device on the tail head to measure subsequent mounting activity. In U.S. Pat. No. 5,566,679, the use of multiple color coded mechanical detectors to detect multiple mounts is described. If a second detector is triggered by a standing mount at a date subsequent to the triggering of a first detector, especially when occurring approximately 21 days following the first insemination, the cow is presumed to have not conceived from the first insemination or is presumed to have lost her pregnancy and needs to be inseminated again. This patent describes the use of multiple detectors of different colors to identify multiple mounts. It does not describe the use of multiple colors in a single device to detect multiple standing mounts.

The use of an estrus detection device to measure mounting activity subsequent to the initial detection of heat and insemination highlights the importance of distinguishing between a mount and a standing mount. A cow that is pregnant may be mounted temporarily but will almost never maintain a standing mount. Methods, such as chalking, that don't distinguish between mounts and standing mounts may lead herdsmen to believe a pregnant cow is open and decide that she should be inseminated again. This is the worst possible course of action. Not only is expensive semen wasted during the second insemination, the previously established pregnancy can be lost as well. On the other hand, if the second detector attached to the tail head of the cow is not triggered at a later date, the cow is presumed to be pregnant. Strictly speaking, an untriggered detector indicates only that a cow has not shown signs of standing heat, not that she is pregnant. Non-pregnant cows that are not cycling due to hormone imbalances may not exhibit standing heats as well. In any case, the lack of mounting behavior as indicated by an untriggered detector can be an important management tool in a dairy breeding program.

Despite numerous and long felt attempts to accurately detect standing heat for the purpose of guiding the timing of artificial insemination, none of these prior art approaches has satisfactorily solved the problem of how to reliably and cost-effectively detect estrus. The limitations associated with the current estrus detection devices include the high cost of the devices themselves and the need to place a second detector on the same cow if mounting activity subsequent to the initial insemination is to be measured. Because of limitations and inadequacies, such as indicated above, the prior art estrus detection systems have had limited success in the cattle and dairy industries.

There remains a strong need for a reliable, economical and easy-to-use apparatus for identifying multiple estruses in cattle and other animals exhibiting standing heat behavior.

SUMMARY OF THE INVENTION

The present invention is an apparatus and method for indicating the onset of behavioral estrus in cattle. The apparatus is comprised of a first fluid storage reservoir containing a colored indicator fluid connected by a reservoir outlet or capillary to a timing chamber which empties into a wicking means. The apparatus also includes a second fluid storage reservoir that is initially disabled but that can be subsequently enabled. This second fluid storage reservoir contains an indicator fluid which is different in color from the indicator fluid in the first fluid storage reservoir. The two fluid storage reservoirs and timing chamber are housed inside a plastic bubble coated with wicking means, preferably flocked cotton, on the inside, all affixed to an animal attachment means which is glued to the tail head of an animal to detect one or more standing mounts. When the apparatus is first glued to the tail head of an animal, the first indicator fluid in the first fluid storage reservoir is in fluid communication with the reservoir outlet and the timing chamber. Fluid in the second fluid storage reservoir is not initially in fluid communication with the first fluid storage reservoir or with the timing chamber. The second fluid storage reservoir is disabled and cannot release its colored fluid into the timing chamber and wicking means until enabled. The disabled second fluid storage reservoir is preferably enclosed within the first fluid storage reservoir.

The flow of the first indicator fluid from the first fluid storage reservoir through a capillary to a timing chamber is always enabled or open. With no further modification, a mount will cause dye-colored first indicator fluid to be expressed from the first fluid storage reservoir through the capillary into a timing chamber. If the mount is a standing mount, the fluid will continue to fill the timing chamber until it contacts the adjacent wicking means on the inside surface of the bubble turning it the color of the first indicator fluid.

A second fluid storage reservoir comprising a tube, preferably cellulose acetate butyrate, is sealed at both ends. The seals block the flow of second indicator fluid from the second fluid storage reservoir when the apparatus is first attached to the cow. The second indicator fluid cannot flow out of the second fluid storage reservoir until the reservoir is burst by the application of high pressure, such as can be achieved by squeezing the tube with a pair of pliers. Pressure with pliers to break an end seal of the second fluid storage reservoir is only applied if the bubble with flock on the inside surface has previously turned the color of the first indicator fluid following a previous standing mount.

In the preferred embodiment, the first indicator fluid in the first fluid storage reservoir is colored with a red dye while the second indicator fluid in the second fluid storage reservoir is colored with a blue dye so that when the blue-colored second indicator fluid contacts the wicking means previously wetted by the red-colored first indicator fluid, it turns almost black. Any combination of colors that allows a herdsman to distinguish between the color of the bubble following the first standing mount and a subsequent standing mount following enablement of the second fluid storage reservoir is acceptable.

The use of this novel and surprising invention in managing a breeding program can save time and money. When a first standing mount is detected by observing a plastic bubble with flock on the inside surface turning red, the color of the first indicator fluid, the cow is inseminated. A short period after the animal is inseminated, an end seal of the second fluid storage reservoir is burst by applying pressure with a pair of pliers through the flocked bubble, thereby releasing the second indicator fluid into the first fluid storage reservoir where it mixes with any residual first indicator fluid. If the flocking on the inside surface of the plastic bubble subsequently turns almost black, particularly 21 days after the first insemination, the herdsman would infer that the cow to which the device is affixed is not pregnant and needs to be inseminated once again. If the flock on the inside of the clear plastic bubble does not turn almost black but remains red for a period in excess of 21 days following the bursting of the second fluid storage reservoir, the herdsman would infer that the cow has not been in standing heat at any time following the first standing heat. A flocked bubble that remains colored with only the first indicator fluid does not indicate the cow is pregnant. It just indicates that she has not returned to standing heat. This can occur either due to the cow being pregnant or to a non-cycling cow.

This surprising and novel invention controlling the flow of different colored indicator fluids from two fluid storage reservoirs in a single device allows a herdsman to detect two separate and distinct standing mounts by attaching just one patch assembly to the tail head of a cow. This saves the cost of a second patch assembly. Equally important, it saves the herdsman the time and effort of attaching a second patch assembly to the tail head of the cow.

OBJECTS AND ADVANTAGES

Accordingly, it is an object of the invention to save the time and cost of applying a second heat detection patch assembly to an animal in order to detect a second or subsequent standing heat. Each detector patch assembly of the present invention is configured with two fluid storage reservoirs, each with an indicator fluid of a different color, with flow of the first indicator fluid initially enabled and the flow of the second indicator fluid initially disabled. The closed second fluid storage reservoir can be burst or enabled at any time, but preferably following the initial detection of a standing mount by the cow as the flocking on the inside surface of the clear plastic bubble is turned the color of the first indicator fluid that is expressed from the first fluid storage reservoir. Any subsequent flow of second indicator fluid from the fluid storage reservoir through the capillary into the timing chamber and then into the flocking which coats the inside surface of the clear plastic bubble would indicate the cow had been in standing heat again and therefore is not pregnant. If the dye-containing second indicator fluid never fills the timing chamber and never contacts the flocked inside surface of the clear plastic bubble, the herdsman would infer that the animal has not exhibited a second standing heat and therefore is pregnant or is not cycling. Either outcome is important to the herdsman as he seeks to maximize the reproductive performance of the herd.

Another object of the invention is to distinguish between a first standing mount and subsequent standing mounts by means of different colored indicator fluids being used in each of the two fluid storage reservoirs contained inside a single bubble.

Other features and advantages of the present invention will become apparent from the following detailed description, taken in conjunction with the accompanying figures, that illustrate by way of example, the principles of the instant invention.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE PREFERRED EMBODIMENT

It is to be understood that both the foregoing general description and the following detailed description are exemplary and explanatory only and are not restrictive of the invention as claimed. The present invention provides a heat detection patch that can detect multiple heats. It is recognized by those skilled in the art that a broad range of patch assemblies may be practiced in accordance with the presently disclosed invention.

Figure 1:
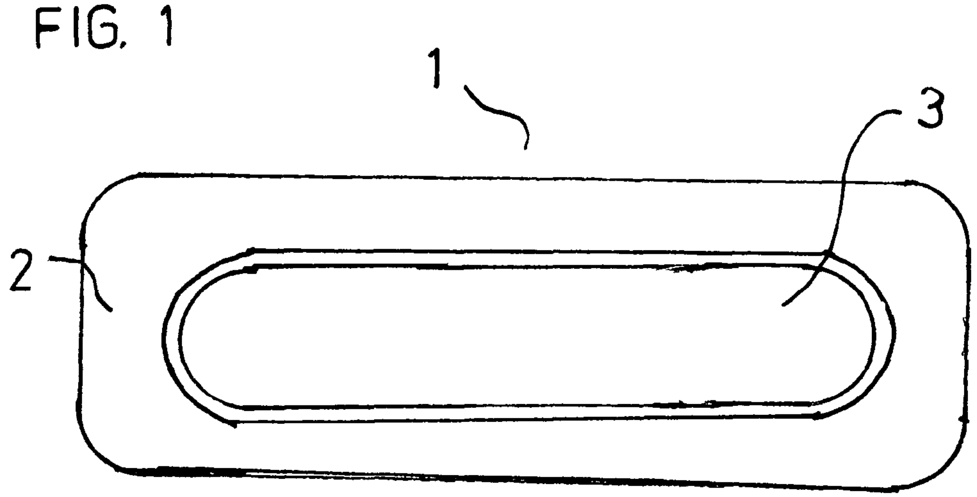
FIG. 1 is a top view of the detection patch assembly.

Referring to FIG. 1, the preferred embodiment of the heat detection patch assembly 1 comprises the animal attachment means 2 that is affixed to the tail head of a cow and a flocked plastic bubble 3 that is attached to animal attachment means 2.

Figure 2:
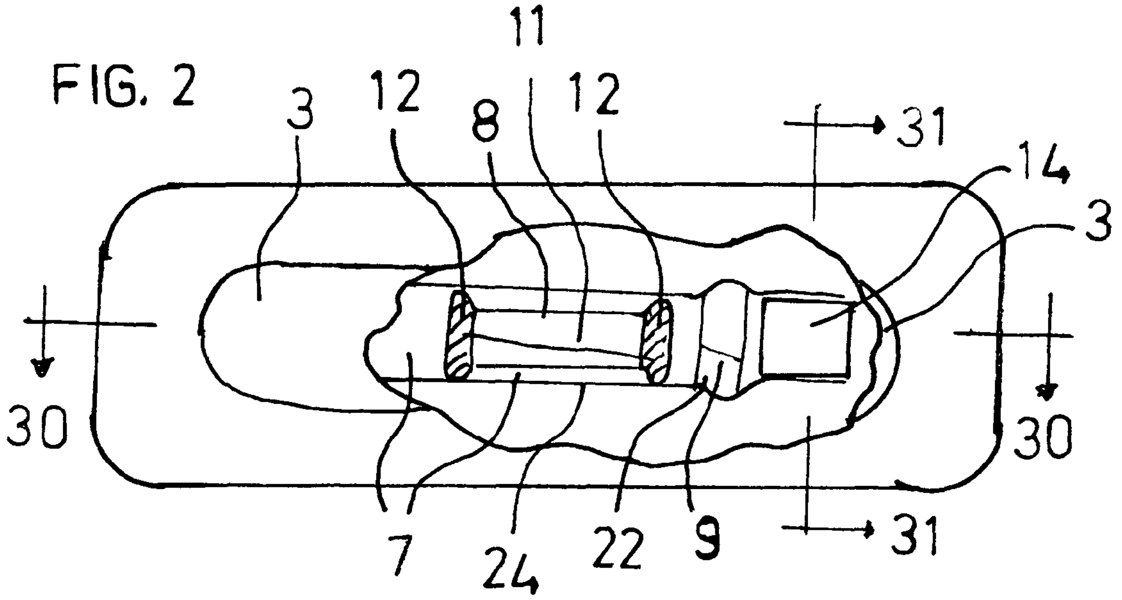
FIG. 2 is a partial cross-sectional top view of the preferred embodiment of the heat detection patch assembly.

The partial cross-sectional top view of FIG. 2 shows bubble 3 enclosing first fluid storage reservoir 7 connected to timing chamber 14 by capillary 9, and second fluid storage reservoir 8 contained wholly within first fluid storage reservoir 7. First fluid storage reservoir 7 has a seal end 22 between it and timing chamber 14. Capillary 9 is located within the seal end 22 and places first fluid storage reservoir 7 in continuous fluid communication with timing chamber 14. First fluid storage reservoir is formed from flexible vinyl tubing 24, such as Tygon® that is preferably 6.5 millimeters (0.25 inches) inside diameter and 8 millimeters (0.3125 inches) outside diameter. Second fluid storage reservoir 8 is formed from a plastic tubing with semi-rigid walls, such as cellulose acetate butyrate, preferably having a wall thickness of 0.38 millimeter (0.015 inches) and an outside diameter of 5.6 millimeters (0.218 inches). Second fluid storage reservoir 8 has two sealed ends 12. Filament 11 runs the length of the second fluid storage reservoir 8 to facilitate satisfactory fluid flow along its outside wall. The timing chamber 14 is preferably formed from rigid cellulose acetate tubing that is 4.8 millimeters (0.1875 inches) inside diameter, 6.5 millimeters (0.25 inches) outside diameter and 7.7 millimeters (0.3 inches) in length. First fluid storage reservoir 7 is filled with first indicator fluid comprising a mix of ethylene glycol and water in a ratio of approximately 2:1, a colored dye, preferably red. Second fluid storage reservoir 8 is filled with a second indicator fluid comprising a mix of ethylene glycol and water in a ratio of approximately 2:1, colored with a dye, preferably blue.

Figure 3:
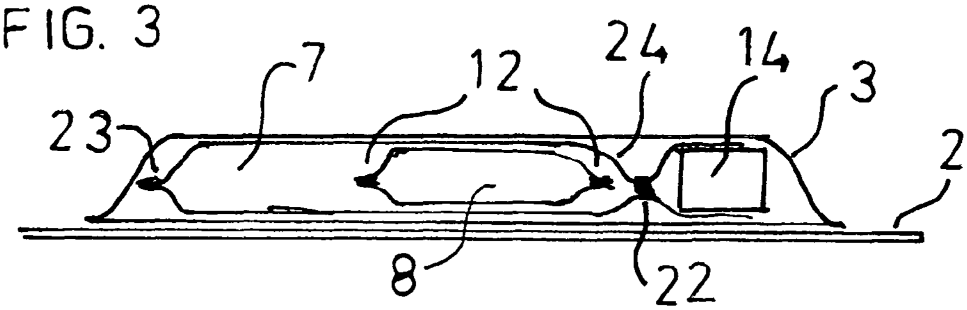
FIG. 3 is a cross-sectional side view of the heat detection patch assembly in FIG. 2, taken along the line 30-30 of FIG. 2.

FIG. 3 shows flocked plastic bubble 3, preferably vinyl, attached to animal attachment means 2. The inside surface of bubble 3 that is adjacent to timing piece 14 contains flocking, such as cotton flocking. The flocking on the inside surface of bubble 3 wicks fluid that is expelled from timing chamber 14 along the entire length of bubble 3, turning it the color of the dye in the indicator fluid. The flexible bubble and the wicking means may be separated. Flexible plastic tubing 24 forms first fluid storage reservoir 7, with seal 22 located between it and timing chamber 14, and seal 23 closing the distal end of the reservoir. Second fluid storage reservoir 8 is situated within first storage reservoir 7, and is sealed at each end with seals 12. As pressure from a first standing mount is placed on collapsible first fluid storage reservoir 7, first indicator fluid contained therein is expressed through capillary 9 into timing chamber 14. Approximately 3 to 4 seconds of pressure from the mounting cow is required for first indicator fluid to fill timing chamber 14, after which period it spills out the end, contacting the wicking means on the inside surface of bubble 3, turning it the color of the first indicator fluid, preferably red. If the mount is not a standing mount and the cow being mounted bolts, any first indicator fluid from reservoir 7 that is expelled into timing chamber 14 is sucked back in into first fluid storage reservoir 7 as flexible plastic tubing 24 returns to its naturally cylindrical state after mounting pressure is removed. Second fluid storage reservoir 8 remains intact and disabled during a first standing mount that expels first indicator fluid from first fluid storage reservoir 7 into timing chamber 14.

Figure 4:
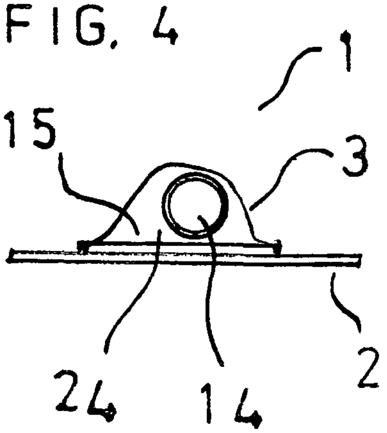
FIG. 4 is a cross sectional end view taken along line 31-31 of FIG. 2.

FIG. 4 is a cross-sectional end view of heat detection patch assembly 1, showing plastic tube 24 enclosing timing chamber 14, all contained within bubble 3 which is attached by seal means to animal attachment means 2. Plastic sheet 15 is interposed between bubble 3 and animal attachment means 2 to function as an adhesive and to provide a closed chamber inside bubble 3. The cotton flocking that serves as a wicking means on the inside surface of bubble 3 cannot be heat sealed directly to animal attachment means 2. Plastic sheet 15, which can melted under heat, is used to seal the two surfaces together. Plastic sheet 15 sealed to bubble 3 also serves to restrict excess evaporation of water from the fluid indicator fluids in the fluid storage reservoirs 7 and 8 and is preferably made of vinyl.

Figure 5:
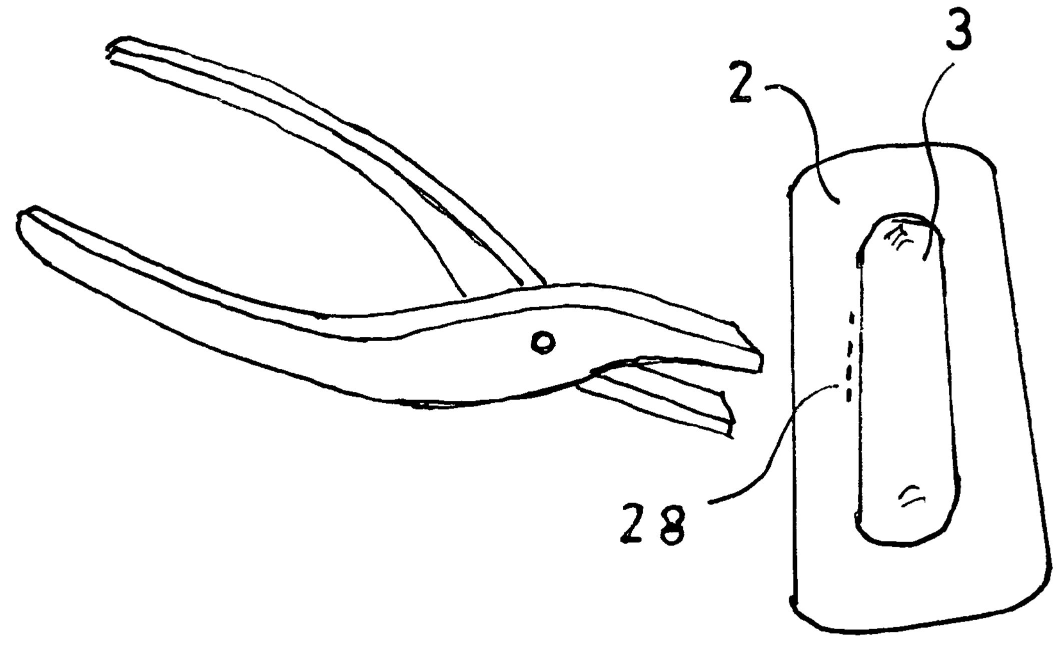
FIG. 5 is a perspective view of the heat detection patch assembly with a pair of pliers positioned to apply pressure to inside reservoirs.

FIG. 5 is a perspective view of the heat detection patch assembly with a pair of pliers positioned to apply pressure to fluid storage reservoirs 7 and 8. One surface of the pliers is placed underneath bubble 3 through slit 38 cut into animal attachment means 2. The opposite surface of the pliers is positioned above bubble 3, so that when the pliers are closed, the pressure is sufficient to burst second fluid storage reservoir 8. Any fluid remaining in first fluid storage reservoir 7 prior to the bursting of second fluid storage reservoir 8 will be expelled to timing chamber 14 while pressure from pliers is applied. Following the bursting of second fluid storage reservoir 8 and the removal of pressure from pliers, any first indicator fluid that was temporarily expelled into the timing chamber will be drawn back into first fluid storage reservoir 7 under partial vacuum where it will mix with the darker fluid from second fluid storage reservoir 8. With thin semi-rigid walls, second fluid storage reservoir 8 cannot collapse under the weight of a standing mount. The walls of this cellulose acetate butyrate tubing will burst only if significant pressure is applied by an implement such as pliers. However, once one of the end seals 12 or walls of second fluid storage reservoir 8 has burst, the walls are thin enough to allow second fluid storage reservoir 8 to collapse under the weight of a subsequent standing mount, expelling most of the fluid into first fluid storage reservoir 7 where it mixes with first indicator fluid. The dye used to color the second indicator fluid should be darker in color than the dye used to color the first indicator fluid so that the flocked inside surface of bubble 3 turns the lighter color first, following the first standing mount, and subsequently turns a darker color second during a subsequent standing mount after second fluid storage reservoir 8 has been burst.

Fluid will continue to wick along the flocking on the inside of bubble 3 even if it has been previously wetted. The color of the bubble being white, red or almost black will help guide breeding decisions by the herdsman. After placement of the heat detection patch assembly on a cow, a white bubble indicates that the cow has not received a first standing mount. A red-colored bubble indicates that the cow has received a standing mount and should be inseminated. Following such insemination, pliers are used to burst second fluid storage reservoir 8, thereby enabling the detector to turn almost black on any subsequent standing mounts. An almost black bubble indicates that the cow is not pregnant from the previous insemination and should be inseminated once again. If the bubble remains red following bursting of second fluid storage reservoir 8, especially for a period in excess of 21 days, the herdsman may conclude that the cow is pregnant or is not cycling, and will take appropriate action at a later time to confirm pregnancy.

The novel and surprising feature of this invention is the sealed second fluid storage reservoir 8 that prevents second indicator fluid from flowing to the timing chamber 14 during the first standing mount. Said sealed second fluid storage reservoir 8 can subsequently be enabled by bursting with pressure from pliers. The ability to apply a heat detection patch with a disabled second fluid storage reservoir to an animal and subsequently enable the flow of second indicator fluid from this second fluid storage reservoir 8 to timing chamber 14 allows heat detection patch 1 to be used to detect two standing heats. This provides for a more economical and cost-effective product that can be used by a larger percentage of the herdsmen that manage the reproductive health of animals.

A herdsman must be able to differentiate between the colors associated with a first standing mount when second fluid storage reservoir 8 remains sealed and any subsequent standing mounts when second fluid storage reservoir 8 has been burst. This can be most easily accomplished by using a color such as red in first indicator fluid stored in first fluid storage reservoir 7 and another color, such as blue, in second indicator fluid stored in second fluid storage reservoir 8. The flocking on the inside of bubble 3 will turn red following a standing mount before second fluid storage reservoir 8 is burst. A subsequent standing mount following the bursting of second fluid storage reservoir 8 will cause blue-colored second indicator fluid mixed with residual red indicator fluid to flow out of timing chamber 14 onto the flocking on the inside surface of bubble 3, turning the previous red color almost black. Any color combinations can be used in the first and second indicator fluids as long as the herdsman can distinguish the difference in color between the first indicator fluid and the subsequent combination of the first and second indicator fluids.

The preferred embodiment shown in the drawings for this invention show a second fluid storage reservoir 8 positioned within first fluid storage reservoir 7. Another configuration for this invention comprises two fluid control elements, each configured like a Kamar, each with its own fluid storage chamber and timing chamber, that are placed side by side inside a single bubble 3. In this configuration one of the reservoir outlets could initially be closed or disabled and subsequently enabled in a manner that falls under the scope of this invention as illustrated in the preferred embodiment.

Another variation of the invention employs a chemical activator that is applied to the flocked inside surface of bubble 3. A chemilluminescent dye could be placed in one or both of the indicator fluids. After filling timing chamber 14 and spilling out, the dye would come into contact with an activator embedded in the flocking, causing the dye to emit a chemilluminescent light.

What is claimed is:

1. A device for detecting standing heats in animals comprising a. at least one first fluid storage reservoir, said first fluid storage reservoir containing a first indicator fluid and having a first reservoir outlet, said first fluid storage reservoir collapsing upon compression to propel said first indicator fluid through said first reservoir outlet and substantially resuming its shape upon release of compression to withdraw said indicator fluid at the first reservoir outlet;

b. at least one timing chamber in fluid communication with said first reservoir outlet, said first reservoir outlet sized to fill said timing chamber with said first indicator fluid during a period corresponding to a minimal standing mount for said animal;

c. wicking means in fluid communication with said timing chamber, said wicking means receiving said first indicator fluid upon compression of said first fluid storage reservoir for a period of time exceeding that required to fill said timing chamber, to record a standing mount;

d. a second fluid storage reservoir containing a second indicator fluid, said second fluid storage reservoir having a closed position in which said second fluid storage reservoir does not communicate with said first fluid storage reservoir or a timing chamber and an open position in which said second fluid storage reservoir is emptied into said first fluid storage reservoir or is in fluid communication with said first fluid storage reservoir or is in fluid communication with a timing chamber, said second fluid storage reservoir in said open position placing said second indicator fluid into said timing chamber upon compression of at least one of said first fluid storage reservoir and said second fluid storage reservoir and in the event that said compression exceeds said period required to fill said timing chamber, second indicator fluid spills from said timing chamber into said wicking means to signal a second standing mount;

e. animal attachment means affixed to at least one of said first fluid storage reservoir, second fluid storage reservoir, timing chamber, and wicking means for attachment to an animal to allow the detection of at least two standing mounts.

2. The device of claim 1 wherein said second fluid storage reservoir is contained in said first fluid storage reservoir.

3. The device of claim 2 wherein said open position of said second fluid storage reservoir is implemented by breaking said second fluid storage reservoir.

4. The device of claim 3 wherein said device records a first standing mount with said second fluid storage reservoir in said closed position and a second standing mount with said second fluid storage reservoir in said open position.

5. The device of claim 1 wherein said first indicator fluid has a first color and said second indicator fluid has a second color, said first indicator fluid and second indicator fluid forming a mixture having a different color than said first color and second color.

6. The device of claim 1 wherein said animal attachment means comprises a base sheet and cover sheet, said base sheet having a bottom surface and a top surface, said bottom surface for receiving adhesive for affixing to said animal, said top surface affixing said first fluid storage reservoir, second fluid storage reservoir, timing chamber and wicking means within said cover sheet.

7. The device of claim 6 wherein said animal attachment means comprises a cover sheet having an inner surface and an outer surface and at least one edge said cover sheet affixed to said base sheet along its edge to form a cover for said at least one first fluid storage reservoir, second fluid storage reservoir, timing chamber and wicking means.

8. The device of claim 7 wherein said cover sheet has at least one transparent area for viewing said wicking means.

9. The device of claim 7 wherein said wicking means is an absorbent material affixed to or retained between said inner surface of said cover sheet and said top surface of said base.

10. The device of claim 9 wherein said cover sheet has a tool area for compression in which a bursting force can be placed on said second fluid storage reservoir that is contained in said first fluid storage reservoir.

11. The device of claim 1 wherein said wicking means is selected from the group consisting of flocking, cloth, absorbent filler, and batting.

12. A method for detecting standing heats in animals comprising the steps of:

providing a device for detecting standing heats in animals comprising:

a. at least one fluid storage reservoir, said fluid storage reservoir containing a first indicator fluid and having a first reservoir outlet, said first fluid reservoir collapsing upon compression to propel said first indicator fluid through said first reservoir outlet and substantially resuming its shape upon release of compression to withdraw said indicator fluid at the first reservoir outlet;

b. at least one timing chamber in fluid communication with said first reservoir outlet, said reservoir outlet sized to fill said timing chamber with said first indicator fluid during a period corresponding to a standing mount for said animal;

c. wicking means in fluid communication with said timing chamber, said wicking means receiving said first indicator fluid upon compression of said first storage reservoir for a period of time exceeding that required to fill said timing chamber, to record a standing mount;

d. a second fluid storage reservoir containing a second indicator fluid, said second fluid reservoir having a closed position in which said second reservoir does not communicate with said first reservoir or a timing chamber and an open position in which said second reservoir is emptied into said first reservoir or is in fluid communication with said first reservoir or is in fluid communication with a timing chamber, said second reservoir in said open position placing said second indicator fluid into said timing chamber upon compression of at least one of said first reservoir and said second reservoir and in the even that said compression exceeds said period required to fill said timing chamber, second indicator fluid spills from said timing chamber into wicking means to signal a second standing mount;

e. animal attachment means affixed to at least one of said first fluid storage reservoir, second fluid storage reservoir, timing chamber, and wicking means for attachment to an animal to allow the detection of at least two standing mounts wherein said device is used for detecting standing heats in cows and other animals.

13. The method of claim 12 wherein said second fluid reservoir is contained in said first fluid storage reservoir.

14. The method of claim 13 wherein said open position is implemented by breaking said second reservoir.

15. The method of claim 12 wherein said device records a first standing mount with said second fluid storage reservoir in said closed position and a second standing mount with said second fluid storage reservoir in said open position.

16. The method of claim 12 wherein said first indicator fluid has a first color and said second indicator fluid has a second color, said first indicator fluid and second indicator fluid form a mixture having a different color than said first color and said second color, said second standing mount recorded in said wicking material as said different color.

17. The method of claim 12 wherein said animal attachment means comprises a base sheet and cover sheet, said base sheet having a bottom surface and a top surface, said bottom surface for receiving adhesive for affixing to said animal, said top surface affixing said first fluid storage reservoir, second fluid storage reservoir, timing chamber and wicking means within said cover sheet, said method further comprising the step of gluing said device to said animal.

18. The method of claim 17 wherein said animal attachment means comprises a base and a cover sheet, said cover sheet having an inner surface and an outer surface and at least one edge of said cover sheet affixed to said base sheet along its edge to form a cover for said first fluid storage reservoir, second fluid storage reservoir, timing chamber, and wicking means.

19. The method of claim 17 wherein said cover sheet has at least one transparent area for viewing said wicking means said method further comprising the step of observing said wicking means through said transparent area.

20. The method of claim 19 wherein said wicking means is an absorbent material affixed to or retained between said inner surface of said cover sheet and top surface of said base.

21. The method of claim 20 wherein said wicking means is selected from the group consisting of flocking, cloth, absorbent filler, and batting.

* * * * *